US006763286B2

(12) United States Patent
Metelski (10) Patent No.: US 6,763,286 B2
(45) Date of Patent: Jul. 13, 2004

(54) STAND

(75) Inventor: Andrzej Metelski, Romanshorn (CH)

(73) Assignee: Leica Microsystems (Schweiz ) AG, Heerbrugg (CH)

( * ) Notice: Subject to any disclaimer, the term of this patent is extended or adjusted under 35 U.S.C. 154(b) by 443 days.

(21) Appl. No.: 09/965,195

(22) Filed: Sep. 27, 2001

(65) Prior Publication Data

US 2002/0108874 A1 Aug. 15, 2002

(30) Foreign Application Priority Data

Sep. 28, 2000 (CH) .............................................. 1898/00

(51) Int. Cl.[7] .......................... G05B 13/00; G01M 1/38
(52) U.S. Cl. ..................... 700/279; 248/127; 248/162.1
(58) Field of Search ....................... 700/279; 206/316.1, 206/316.2, 316.3; 248/550, 651–657, 676, 121–128, 158–162.1, 364

(56) References Cited

U.S. PATENT DOCUMENTS

| | | | | | |
|---|---|---|---|---|---|
| 3,891,301 A | * | 6/1975 | Heller | ......................... | 359/384 |
| 5,213,293 A | * | 5/1993 | Muentener et al. | .... | 248/123.11 |
| 5,667,186 A | * | 9/1997 | Luber et al. | ................. | 248/550 |
| 5,818,638 A | * | 10/1998 | Nakamura | ................... | 359/384 |
| 6,129,319 A | * | 10/2000 | Metelski | .................. | 248/123.2 |
| 6,471,165 B2 | * | 10/2002 | Twisselmann | ......... | 248/123.11 |
| 6,532,108 B1 | * | 3/2003 | Pensel | ......................... | 359/384 |
| 6,539,333 B1 | * | 3/2003 | Metelski | ..................... | 702/173 |
| 6,543,914 B2 | * | 4/2003 | Sander | ....................... | 362/401 |
| 6,592,086 B1 | * | 7/2003 | Sander | .................. | 248/123.11 |
| 2002/0108874 A1 | * | 8/2002 | Metelski | .................. | 206/316.1 |
| 2002/0121577 A1 | * | 9/2002 | Metelski | ................ | 248/123.11 |
| 2002/0121578 A1 | * | 9/2002 | Metelski | .................. | 248/125.2 |

FOREIGN PATENT DOCUMENTS

| EP | 1193438 A2 | * | 4/2002 |
| JP | 2002228938 A | * | 8/2002 |
| WO | WO 97/13997 | | 4/1997 |

* cited by examiner

Primary Examiner—Maria N. Von Buhr
(74) Attorney, Agent, or Firm—Hodgson Russ LLP (57) ABSTRACT

A stand having an automatically correctable balancing system and balancing mechanisms electrically controlled by a computer (10). Replaceable accessories can be joined to a component (9) movably joined to the stand (6). Associated with the computer (10) are a calculation program and an information system that, by means of a reading device, reads correction information from data media of the accessories and conveys it to the computer.

29 Claims, 12 Drawing Sheets

STAND

CROSS REFERENCE TO RELATED APPLICATIONS

This invention claims priority of the Swiss patent application 2000 1898/00 filed Sep. 28, 2000 which is incorporated by reference herein.

FIELD OF THE INVENTION

The invention concerns a stand having a balancing device.

BACKGROUND OF THE INVENTION

Stands, in particular for surgical microscopy or the like, should be properly balanced so that the microscope can be pivoted, lifted, lowered, and moved in space with relatively little application of force. The existing art discloses several methods for balancing, including semi-automatic or automatic balancing methods, in which a balance status is measured via a force or displacement sensor and an electrically controlled balancing action is performed on the basis of that measurement.

The term "electrically controlled balancing action" is to be understood, for example, as the activation of an electric drive that displaces balancing weights. One example of such a balancing device has been disclosed in the applicant's PCT international patent application WO-A-97/13997.

The conventional and hitherto published balancing systems with electrical or electronic assistance are based on the assumption that the imbalance is measured as a physical magnitude, and the balancing operation is performed on the basis of the measurement result. This requires corresponding force measurement sensors and a corresponding measurement operation; only after that can the balancing operation take place. Because they are located on moving systems, such force measurement sensors and the electronic amplifiers necessary for them are usually complex and expensive. Leaving this aside, the balancing operation is always reactive, since first measurement occurs and then balancing. With some stands of the existing art with semi-automatic balancing, for example, after an accessory change a button on the stand that initiates the balancing operation must be pressed.

With such systems, a certain time therefore also elapses before the balanced state is achieved.

The fully automatic balancing systems described in the literature have, compared with the button-controlled systems, the (sometimes undesirable) characteristic that they balance out a stand even when the balancing operation is not desired. For example, when the stand is balanced and a surgeon then leans against or holds onto the microscope, in fully automatic systems this can immediately result in a balancing operation. When the bracing forces on the microscope are released, e.g. when the hands are released or the head pulled back, this balance operation can result in a severe imbalance. This must first be detected and compensated for by another balancing operation. During this period the microscope is not fully usable by the surgeon, thus in some circumstances preventing him or her, during this detection and balancing operation, from continuing the surgical procedure until this new balancing operation is complete. In the case of an automatically operating stand of the applicant (OHS), this balancing is therefore performed not continuously but only after switching into balancing mode. But if an assistant adjusts or replaces accessory parts during the procedure, the microscope is then at first no longer balanced. To allow the surgeon to work unhindered, another time-consuming balancing action (switching over into balancing mode) is necessary, and the surgery must be interrupted during this period.

The Möller-Wedel company has proceeded from another consideration in its stand design. First a mechanical balance is achieved. If components on the microscope are then replaced, this balance is not disturbed at all but rather adjustments intended to re-establish balance are performed on the components themselves, or on other components present on the microscope. For example, the assistant's tube is pivoted so that a balanced state is achieved.

This is often unsatisfactory, however, since a position that does not conform to the desired working position is thereby established.

SUMMARY OF THE INVENTION

It is the object of the invention to find a new balancing system which dispenses with complex and expensive force or displacement sensors and performs a balancing operation, avoiding any interruption of the surgical procedure, as immediately and quickly as possible as soon as any modification to the accessories of the microscope occurs, without previously performing a measurement operation of physical magnitudes such as forces, deformations, or the like; and in which an undesired balancing operation resulting from bracing forces, as described above, is prevented.

The particular aspect of the present invention is a completely new philosophy: there is no intention to measure physical forces or displacements (deformations) that provide some information about the balance state; instead a complete computer-assisted mathematical model of the stand is provided. The addition or removal of components to or from this model (addition or removal of accessories to or from the microscope or change in the position of essential components) causes the computational model to be correspondingly modified; the corresponding change in the model is taken into account computationally, and on the basis of the computational model the control commands for the electrical activation of counterweights are initiated.

As compared to the existing more or less intelligent balancing systems (imbalance is measured by means of intelligence and balanced out by means of an intelligent control system), for the first time according to the present invention an intelligent stand is put into service. The intelligent use of a computer and corresponding programming or calibration means that the stand "knows" its configuration and recognizes any change to its configuration, in order to carry out corresponding balancing actions by means of direct activation of counterweights or the like.

What is provided first of all according to the present invention is therefore a computer that contains a program with which the balance states can be calculated and the absence of balance is ascertained computationally, by the fact that the added or removed components (e.g. accessory parts on the microscope) are entered along with their properties that influence the overall model. This input is preferably accomplished in coded form, so that information about the accessory part added to or removed from the microscope can be entered into the computer, for example manually or by means of a barcode reader or the like.

For example, each accessory part bears a number that the user communicates to the computer via a keypad before installing the component. In accordance with a particular embodiment of the invention, automatic recognition of the accessory parts is provided for in order to speed up this operation. This is accomplished, for example, by way of an automatically readable barcode that is applied to a location on the accessory part that is automatically sensed by a reading device upon installation.

According to a further particular embodiment of the invention, a microchip having the corresponding information written into it (for example, a microchip like that on a check card) is provided instead of a barcode.

Of course magnetic or other data media or the like could also take care of the corresponding information transfer between accessory part and computer. What is favorable with this configuration is that the computer automatically and immediately detects, without further intervention, which accessory parts have been removed from the microscope and which have been added. Since all these components are included in the computational model, the correct balance position of the counterweights can be set directly and immediately.

Balancing thus takes place substantially more quickly than with conventional stands. The intelligence for the actual balancing operation can in fact be reduced (and can thus be cheaper) as compared to the known semi-automatic or automatic balancing systems.

With a configuration according to the present invention, once a balancing operation has been performed it is also not influenced by pressure from the operator's head or hands. Such operations are not even encompassed by the computer or the mathematical model.

A further particular embodiment of the invention provides for the provision, in addition or alternatively to the information-transferring part (chip, barcode, or the like), of angle sensors or displacement sensors which sense the positions of pivotable parts of the accessories and, on the basis of a specific pivot position of said parts, signal to the computer (optionally via the chip) and to the computational model of the balancing system a change that makes possible or triggers a balance correction. In contrast to the force measurement sensor systems used hitherto in balancing systems, angle sensors are very inexpensive; in addition, the demands made on them are not particularly great, since slight changes in the angular position of, for example, a tube do not have a substantial effect on the imbalance of a fully balanced stand.

As part of a development of this inventive embodiment, there is provided for the angle sensor and for the chip connected to it a suitable logic system that continuously supplies the corresponding balance information to the computer. In this case it is not absolutely necessary for the accessory part information to be coded and stored in tabular form in the computer; instead the mathematical model is calculated automatically in each case on the basis of the balance information read in automatically by the respective accessories.

The specific configuration of the stand is not critical for implementation of the actions according to the present invention described above. The assemblage can have parallelogram supports or standard beam supports or the like. Conventional stands can easily be retrofitted with what is proposed according to the present invention, since as a rule only additional data lines and data acquisition elements need to be installed.

As an alternative to data lines and electronically connected systems, accessory parts that can be connected to the computer by means of infrared sensors or other telecommunication devices (for example ultrasound or radio waves) are also conceivable. For example infrared light-emitting diodes or reflectors, for example such as those described in the applicant's European Patent Application EP-A-822 436, can be constructed. In other words, light pulses proceeding from the accessory part communicate their balance characteristics information to the computer via corresponding light pulse receivers.

The invention also makes it possible to develop a standard for accessory parts that permits the universal utilization of accessory parts on different systems having a balance computer according to the present invention. The invention also allows a customer's own accessory parts to be calibrated at the manufacturer's facility by providing there a reference stand on which, by means of conventional balancing system measurement devices, the balance characteristic of the corresponding accessory part is determined and is then coded thereon. This can be accomplished, for example, by way of the barcode, a chip, or another code that is optionally supplied additionally by means of a computer diskette.

Of course the invention is not limited to a pure balancing apparatus corresponding to the above inventive features; on the contrary it also allows for a combination with conventional automatic or semi-automatic balancing systems if advantages for the user may be derived therefrom. What is critical in any event is that by way of the balancing system according to the present invention, optimum and immediate balancing can be effected directly without further measurement operations.

The present invention is also particularly suitable for balancing directly at the optics support, i.e. for pivoting movements of the microscope about a horizontal axis and at least one farther axis that is arranged at an angle to the horizontal axis. For balancing according to the present invention in the context of a pivot support (a pivot support is that component which directly holds the microscope and which gives the microscope mobility in space by way of at least one, as a rule two to three, pivot axes, and which in turn is mounted on supporting elements of the stand) according to the present invention balancing is performed in such a way that by way of the electrical drives, the center-of-gravity axes and the intersection of the pivot axes of the stand are displaced relative to one another in such a way that the intersection of at least two pivot axes (or even three or more pivot axes) ends up at the center of gravity of the microscope or of the microscope having the assemblage joined directly to the microscope.

This balancing action can be brought about by the displacement of counterweights that displace the center of gravity of the microscope or of the assemblage; or by the displacement of pivot axes so that their intersection ends up at the center of gravity; or by displacement of the microscope or the relevant accessory parts relative to the corresponding pivot axes of the microscope, so that its center of gravity is placed on the intersection of the axes.

Optimal balancing of the pivot support exists when the intersection of all the pivot axes is located exactly at the center of gravity of the movable assemblage (microscope with accessories).

In an embodiment, the invention provides in particular for balancing to occur according to the present invention on a stand both in the pivot support and on the other supports.

BRIEF DESCRIPTION OF THE DRAWINGS

The invention will be explained in more detail below with reference to the exemplary embodiments that depict it in exemplary and symbolic fashion. In the drawings.

DETAILED DESCRIPTION OF THE INVENTION

Figure 1:
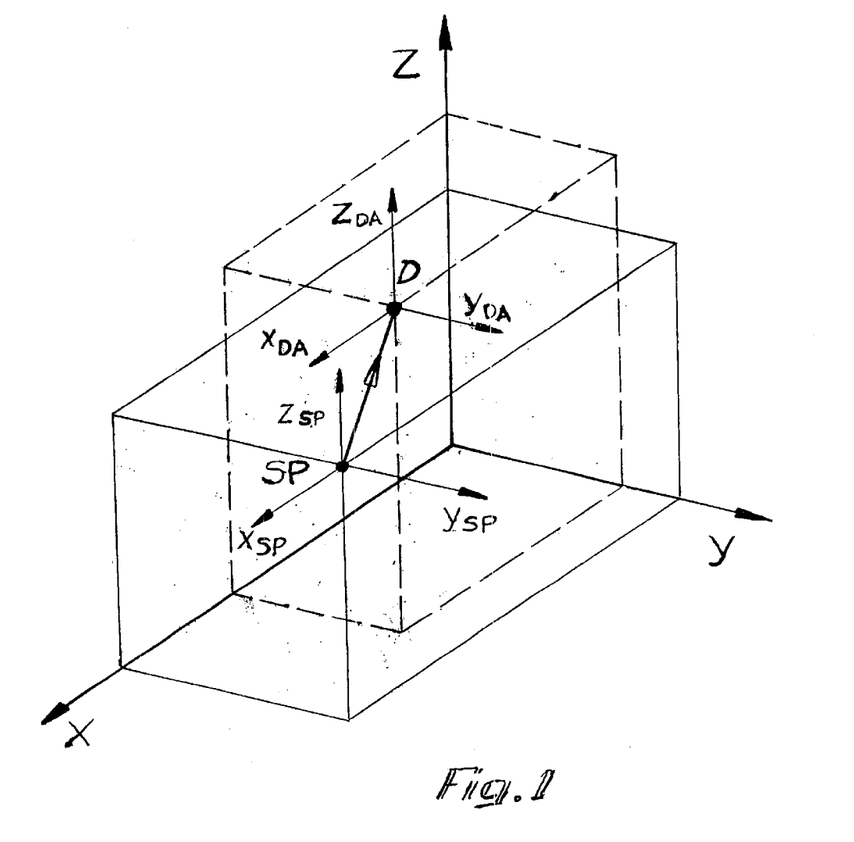
FIG. 1 shows an X-Y-Z coordinate system in which the intersections of the pivot axes and the center-of-gravity axes are displaced with respect to one another.

The computer-assisted relative displacement of intersection D of pivot axes $x_{DA}/y_{DA}$ and $z_{DA}$ and intersection SP of center-of-gravity axes $x_{SP}/y_{SP}$ and $Z_{sp}$ in an X-Y-Z coordinate system of a pivot support is shown in FIG. 1. This relative displacement is necessary so that the system is balanced, can be moved with little effort, and is in equilibrium in every desired operating position.

Figure 2:
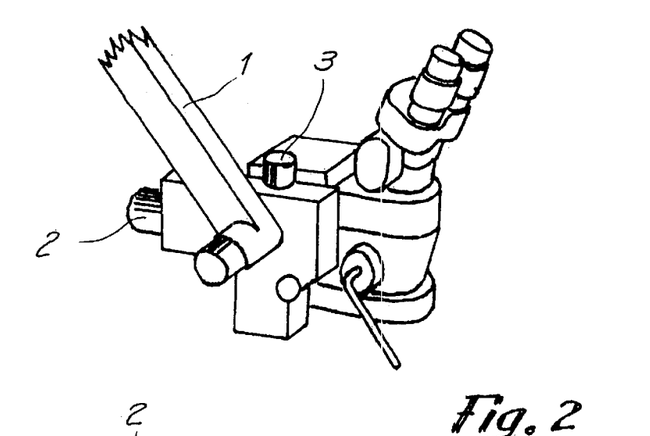
FIGS. 2 through 4 show conventional surgical microscope assemblages having a pivot support and novel balancing drives.
Figure 3:
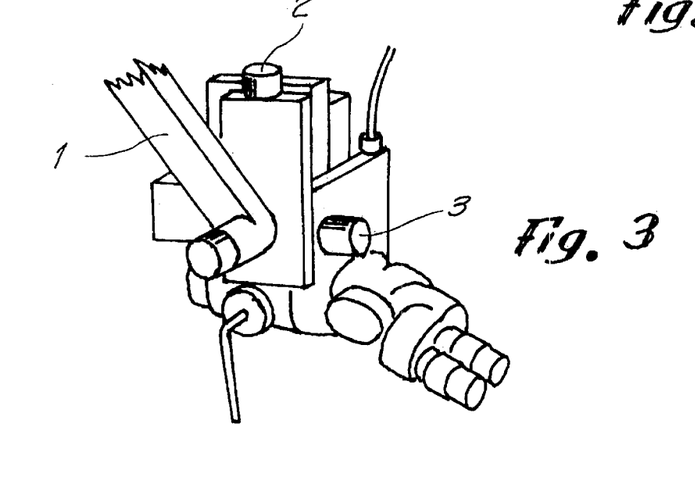
Figure 4:
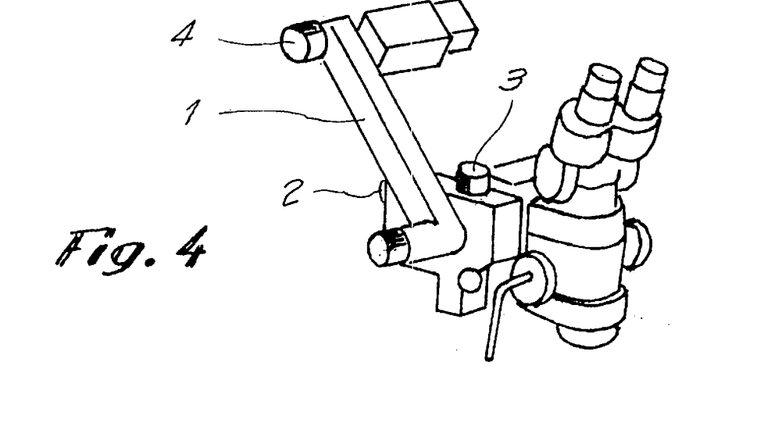

FIGS. 2 through 4 show modified conventional surgical microscopy assemblages having a pivot support 1 and an automatic balancing system that is activated according to the present invention. Located on the microscope, instead of the hand screws hitherto used for balancing, are electric motors 2, 3, and 4 activated by the computer. The computer receives its data via the coding components, which are not visible in FIGS. 2–4 since they are each located in the device attachment region (interface).

Figure 5:
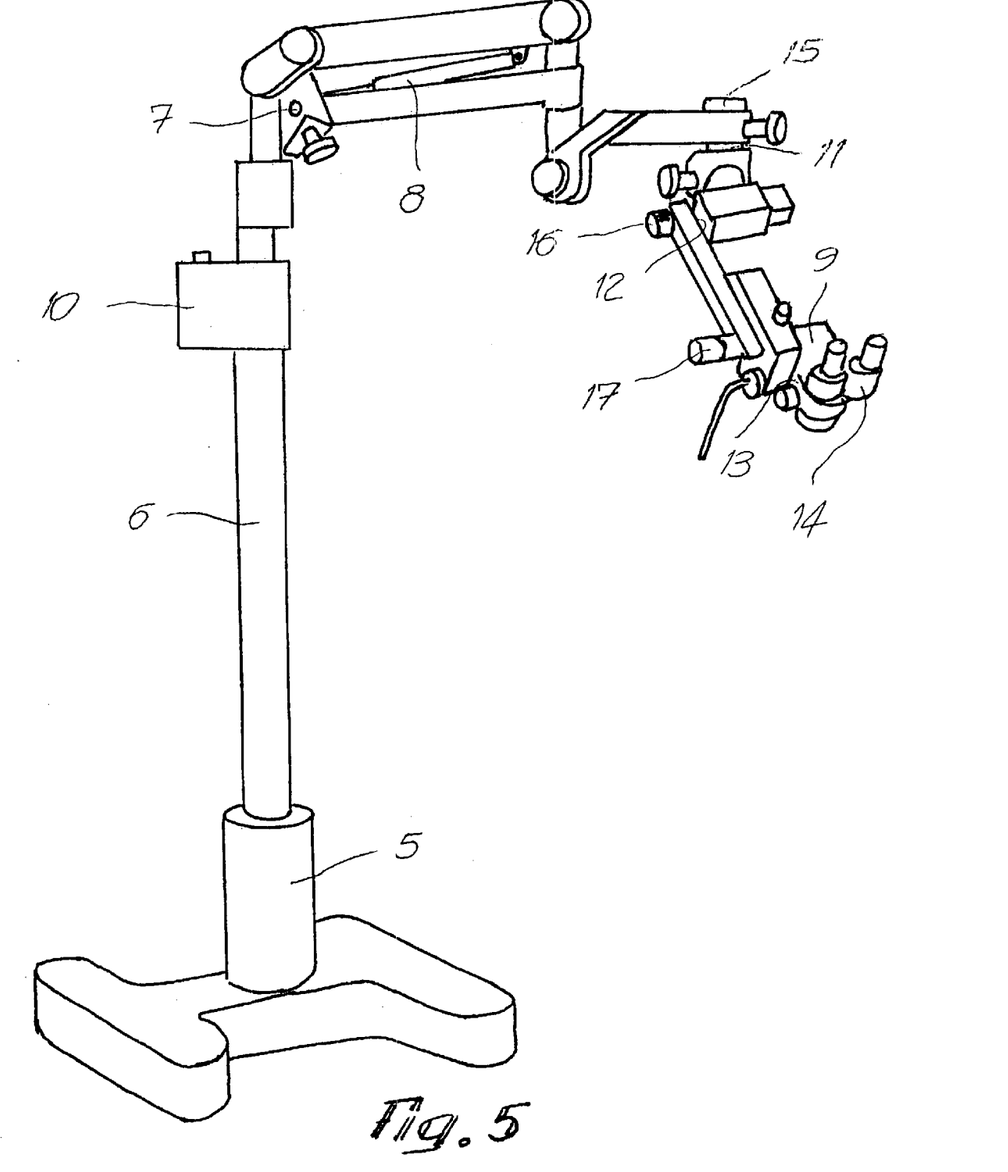
FIG. 5 shows a conventional stand assemblage with internally located coded data at the interfaces.

In the conventional stand assemblage shown in FIG. 5, having a stand foot 5 and support column 6, the one bracing point 7 of a bracing spring 8 is displaced under computer control as a function of weight changes in the region of microscope 9. A computer 10 arranged on support column 6 learns of the weight changes due to the exchange or adjustment of accessory parts by way of the coded data that are automatically forwarded to computer 10 by the respectively added accessory parts (e.g. a swiveling tube) from interfaces 11, 12, 13, and 14. Additional information is received by computer 10 from angle sensors 15, 16, and 17, which are arranged in the region of the joints and detect the respective position of the accessory and forward it to computer 10.

The angle sensors indicated in FIG. 5 are generally not needed in an assemblage having a bracing spring 8 and parallelogram supports, since the change in the position of the components at the end of the parallelogram support does not result in any change in balance. If, however, bracing spring 8 is stiffened or immobilized, or if the parallelogram support is replaced by a simple horizontal beam, the change in angle about the angle sensors shown here also results in changes in balance. On the other hand, no matter what the approach, the aforementioned angle changes result in a change in the tipover resistance of the stand by way of stand foot 5. Angle sensors of this kind may thus also be provided in order to ascertain information regarding tipover resistance and enter it into the balancing system, which warns of imminent tipover of the stand, for example, by means of an alarm signal.

A tipover warning system of this kind constitutes a separate, independent invention, since it can usefully be applied to any surgical microscope stand.

Figure 6:
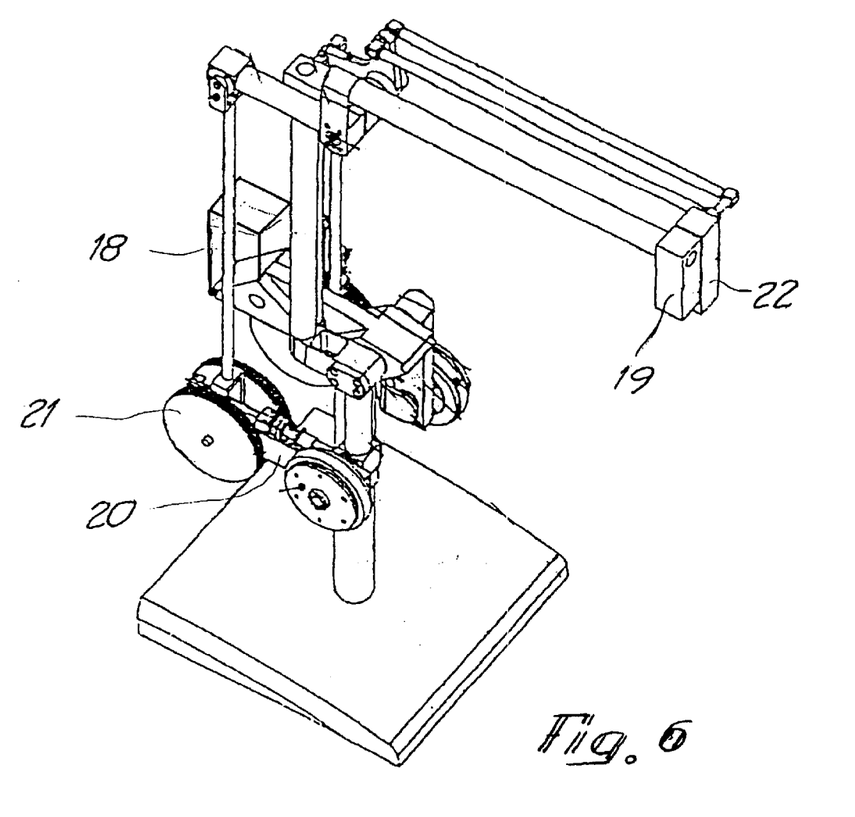
FIG. 6 shows an assemblage corresponding to FIG. 11 of the aforementioned WO-A-97/13997, but having a code reading device and a computer.

The assemblage shown in FIG. 6 corresponds to that in FIG. 11 of the aforementioned WO-A-97/13997. In contrast to the assemblage defined in WO-A-97/13997, an electric motor 20 for displacing counter weight 21 is controlled not by an equilibrium sensor but by a computer 18; computer 18 receives its data in coded form, via a reading device 19, from the accessory parts mounted in front beneath component 22.

Figure 7:
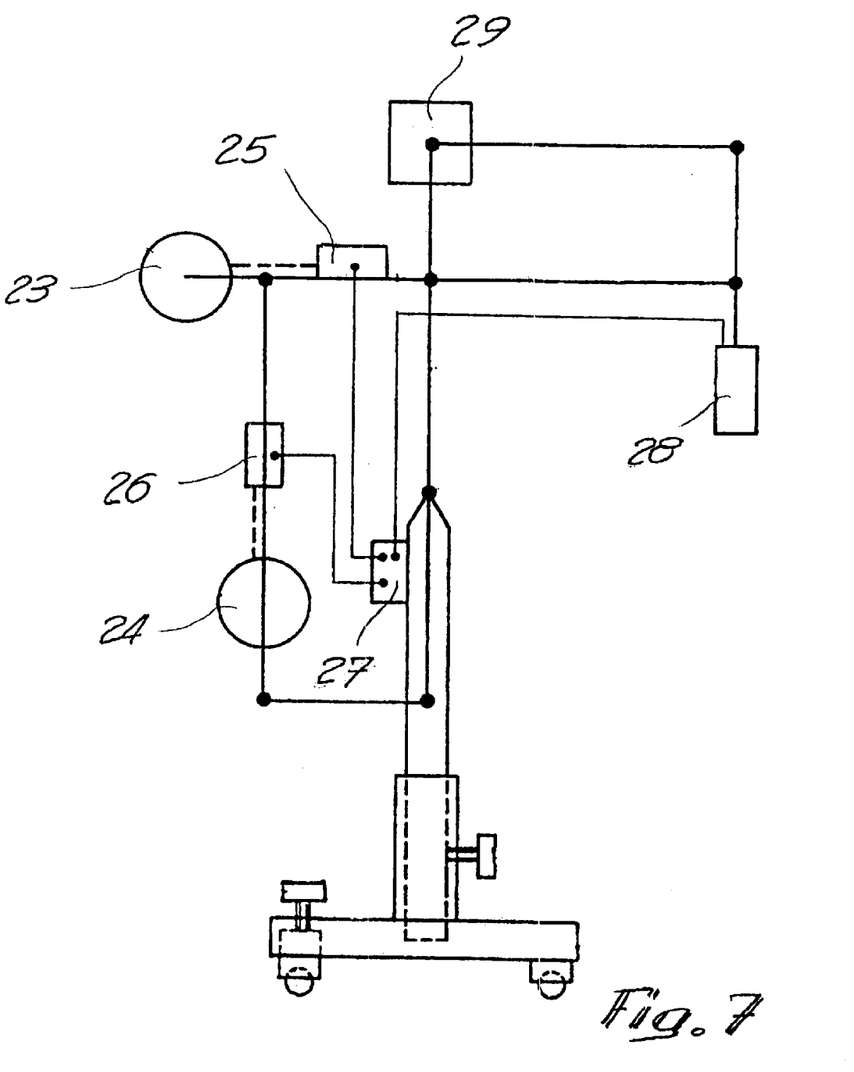
FIG. 7 shows a symbolic stand assemblage having electric motors (positioning motors) which displace the counterweights in computer-assisted fashion.

In the symbolic depiction visible in FIG. 7, counterweights 23, 24 are displaced in computer-assisted fashion by means of electric motors (positioning motors) 25, 26. The data for computer 27 come, according to the present invention, directly from load 28 and/or from an angle sensor 29 via electrical connecting lines.

Figure 8:
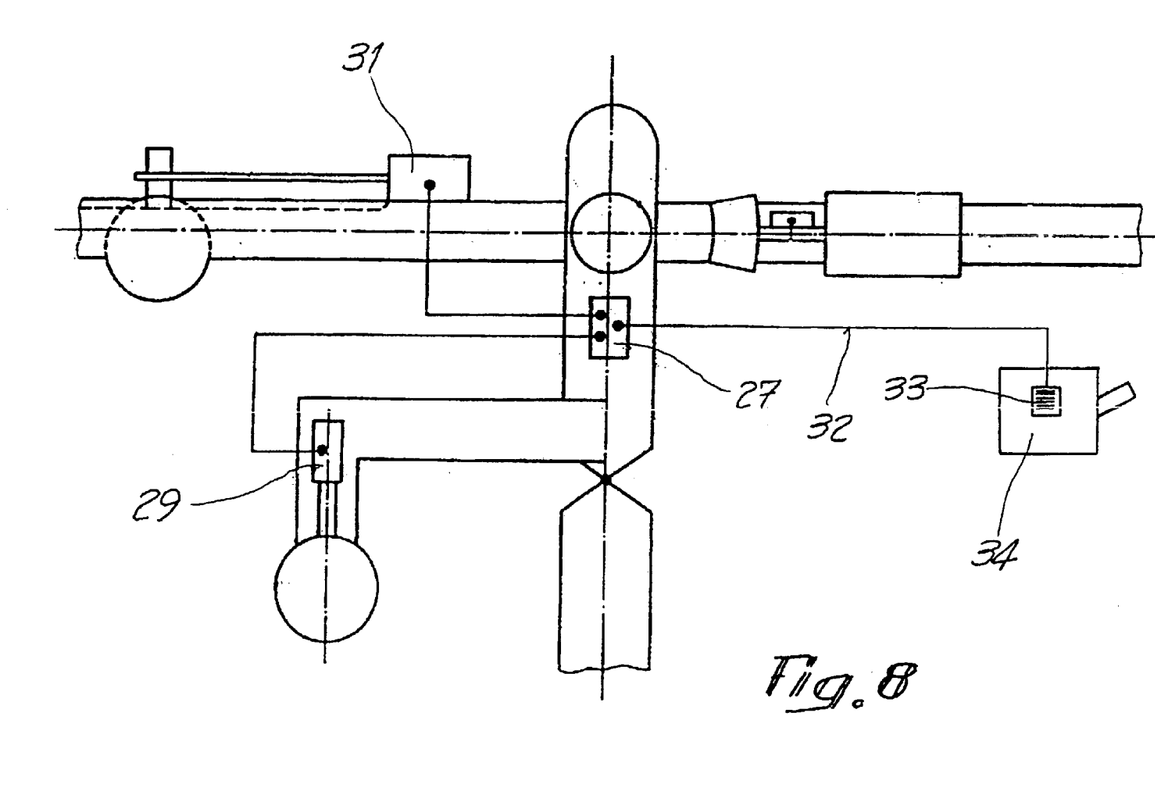
FIG. 8 shows a stand beam with a computer and two counterweights.

The stand assemblage shown in FIG. 8 comprises a computer 27, adjusting motors 31, a control line 32, and (symbolically) a chip 33 on microscope 34 that contains the relevant information for computer 27. Also indicated is an angle sensor 29 that senses pivoting motions about a vertical plane and forwards them to computer 27.

Figure 9:
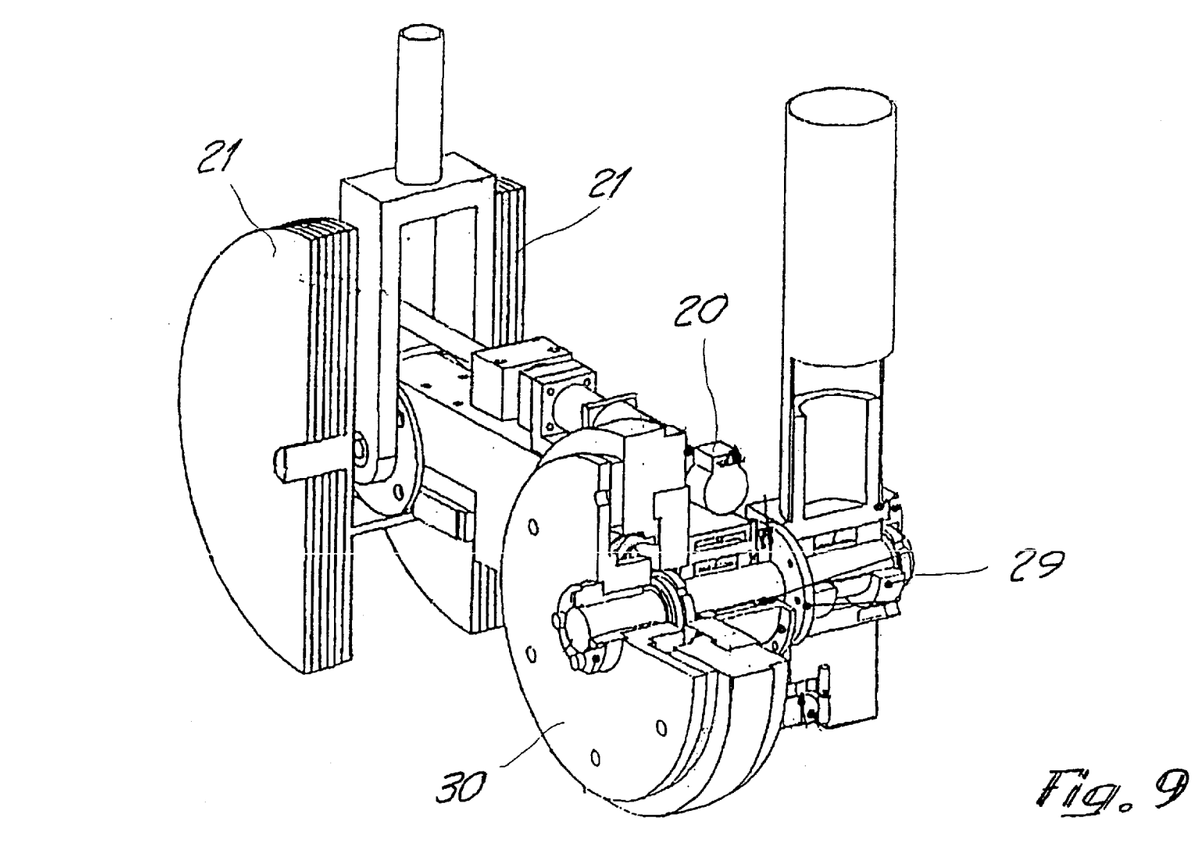
FIG. 9 shows a detail of the assemblage shown in FIG. 6.

FIG. 9 shows a detail of the assemblage of FIG. 6 at enlarged scale. Electric motor 20 for adjusting counterweights 21 is clearly evident here. Also apparent are a conventional brake 30 for retaining a position, and an angle sensor 29 which indicates the pivot position.

Figure 10:
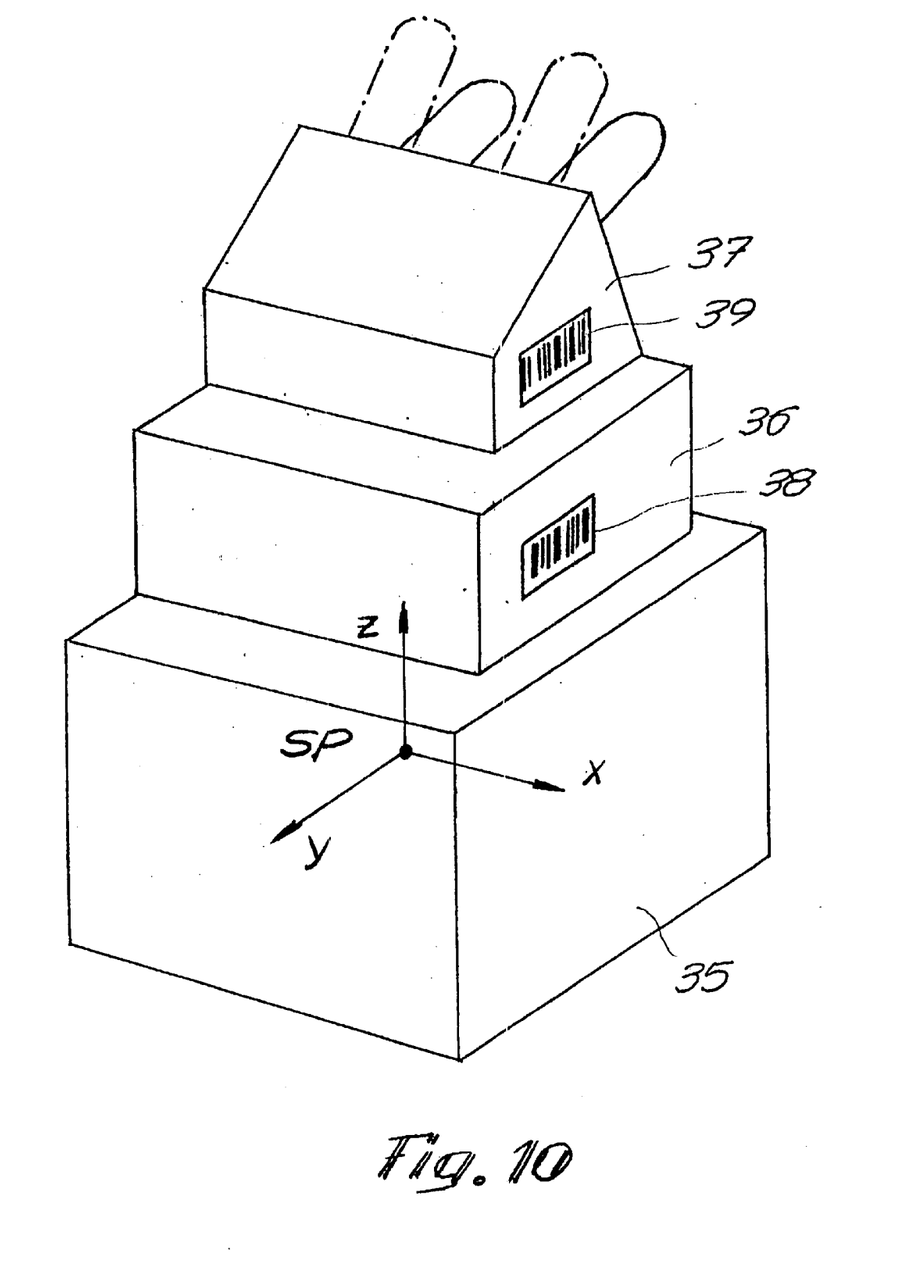
FIG. 10 shows a symbolic depiction of an accessory assemblage with coded data media.

The arrangement depicted in FIG. 10 symbolically shows an assemblage of accessory parts; accessory parts 36 and 37 are detachably joined to a component 35. The addition of accessory parts 36, 37 causes a shift in the overall center of gravity SP of the system. Accessory parts 36, 37 are equipped with data media 38, 39 from which the necessary correction data (which can also be letters or numerical codes) can be read manually or automatically by a reading device and forwarded to the computer.

Figure 11:
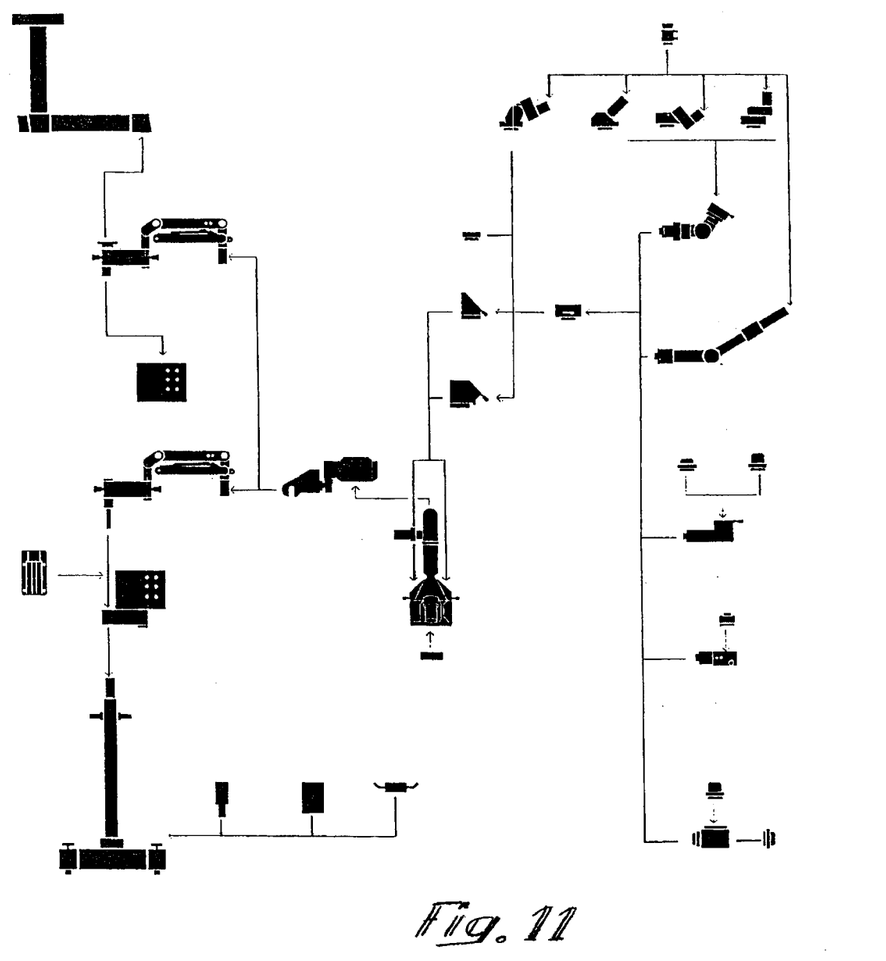
FIG. 11 shows, by way of example, a plurality of accessory parts each of which is coded.

FIG. 11 depicts, by way of example, a plurality of accessory parts that belong to an accessory system. Each accessory part is individually coded and can be used on a surgical microscope individually or in combination with other accessory parts.

Figure 12:
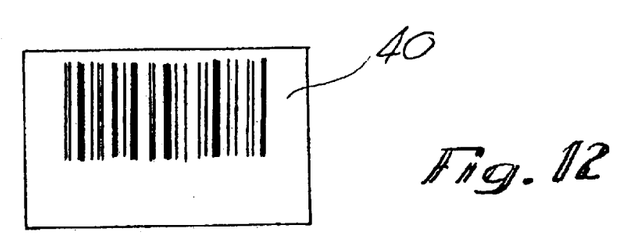
FIGS. 12 and 13 show examples of different variants of data media.

FIG. 12 shows a data medium, equipped with a so-called barcode, for the correction data for the balance control system that are to be applied to the accessory parts. This data medium 40 is configured, for example, as a self-adhesive label.

Figure 13:
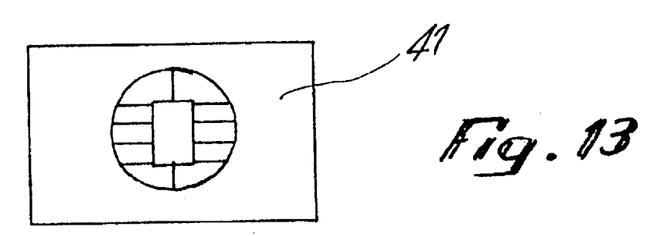

Shown in FIG. 13 is a further data medium 41 having a microchip such as the one used, for example, on credit cards. Microchips of this kind—or also magnetic strips that are also used, for example, on credit cards—can be programmed by the manufacturer of the accessory part, or optionally also later on by the user.

Figure 14:
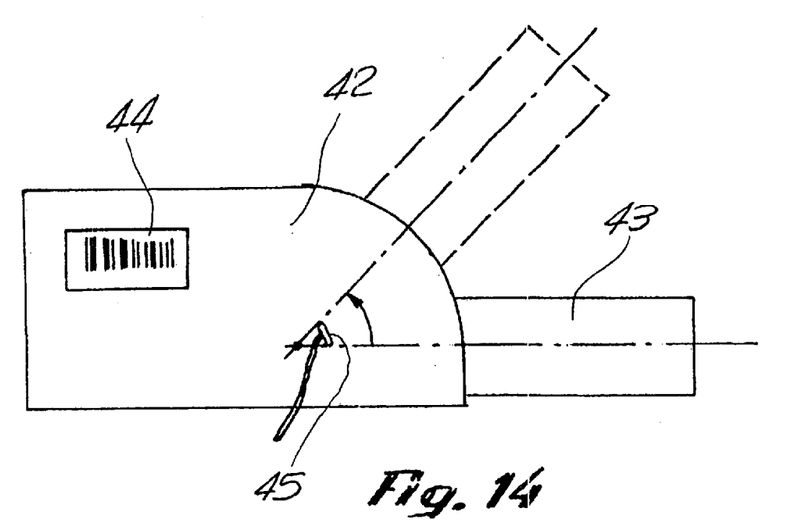
FIG. 14 shows an accessory part with angle sensor and barcode.

Accessory part 42 symbolically depicted in FIG. 14 comprises, for example, a so-called swiveling tube 43, a barcode data medium 44, and an angle sensor 45. Angle sensor 45 serves to sense the respective position of the adjustable swiveling tube 43, which also can influence the balance of the system.

Figure 15:
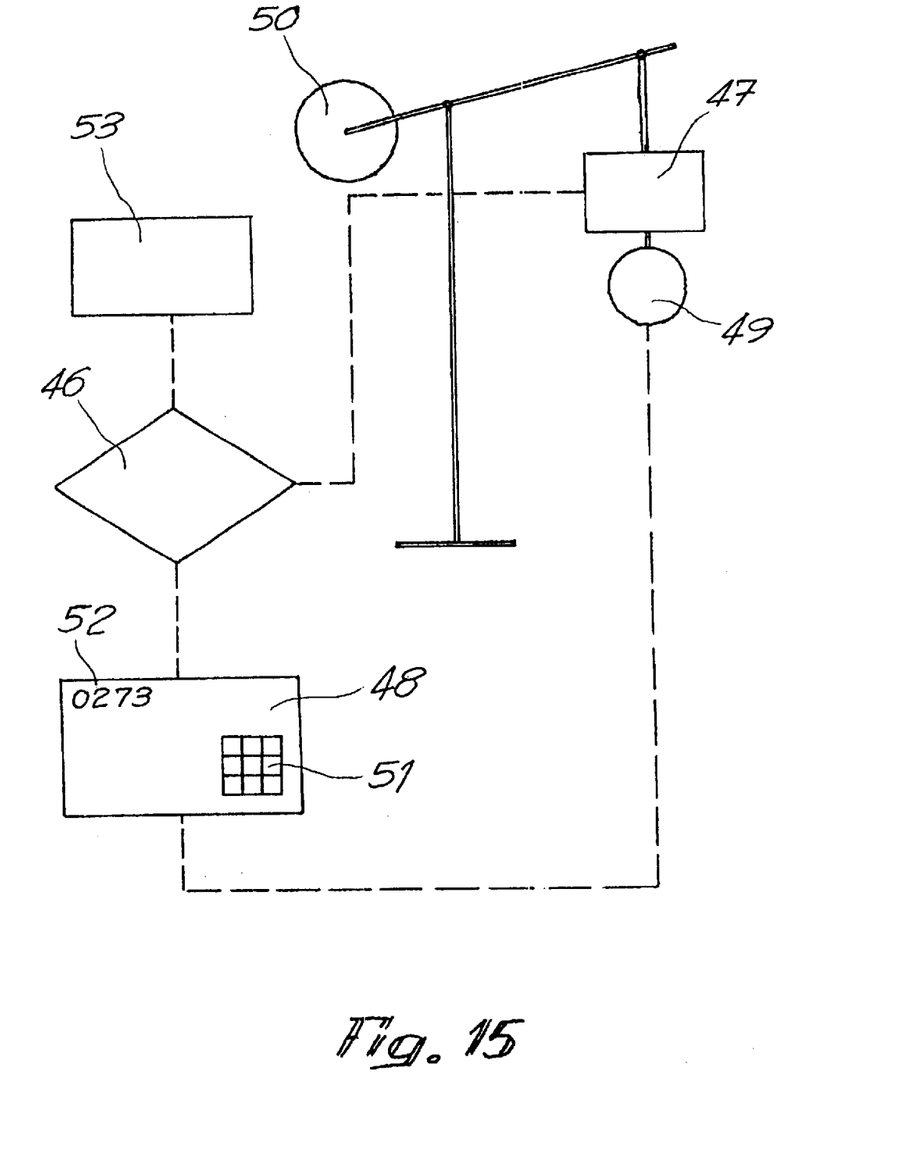
FIG. 15 shows a model of the overall assemblage.

The schematic model of an overall assemblage evident from FIG. 15 shows an information system 46 that conveys to a central computer 48 the fixed data stored on accessory parts 47 as well as any data dependent on the working position of accessory parts 47. This computer 48 determines the necessary correction values and forwards them, as setpoints, to balancing system 49, 50. The balancing system can also simply positionally displace the actual weight, i.e. the microscope or the corresponding component, in order to achieve the balancing effect. The correction data can also be read off from accessory part 47 visually and entered into computer 48 manually via a keypad 51. A digital display 52, for example, can serve to check the values that are entered.

The system can additionally be equipped with an intelligent component 53 (for example a microchip) which can perform queries or, for example, can be used for calibration of new accessory parts.

As an alternative to the aforementioned displacement of counterweights in balancing systems 49 or 50, provision is made according to the present invention for the entire system being balanced to be shifted over the corresponding balance axis, or for the center of gravity to be placed into this corresponding axis. Provision is thus made, for example, for providing on the vertical column, below the mounting point for the transverse beam, an X-Y adjusting unit which modifies the position of the transverse beam relative to the column as soon as the weight in the context of balancing system 49 is modified by the addition of additional components or the removal of such components. This is merely an indication by way of example, intended to illustrate the principle.

Figure 16:
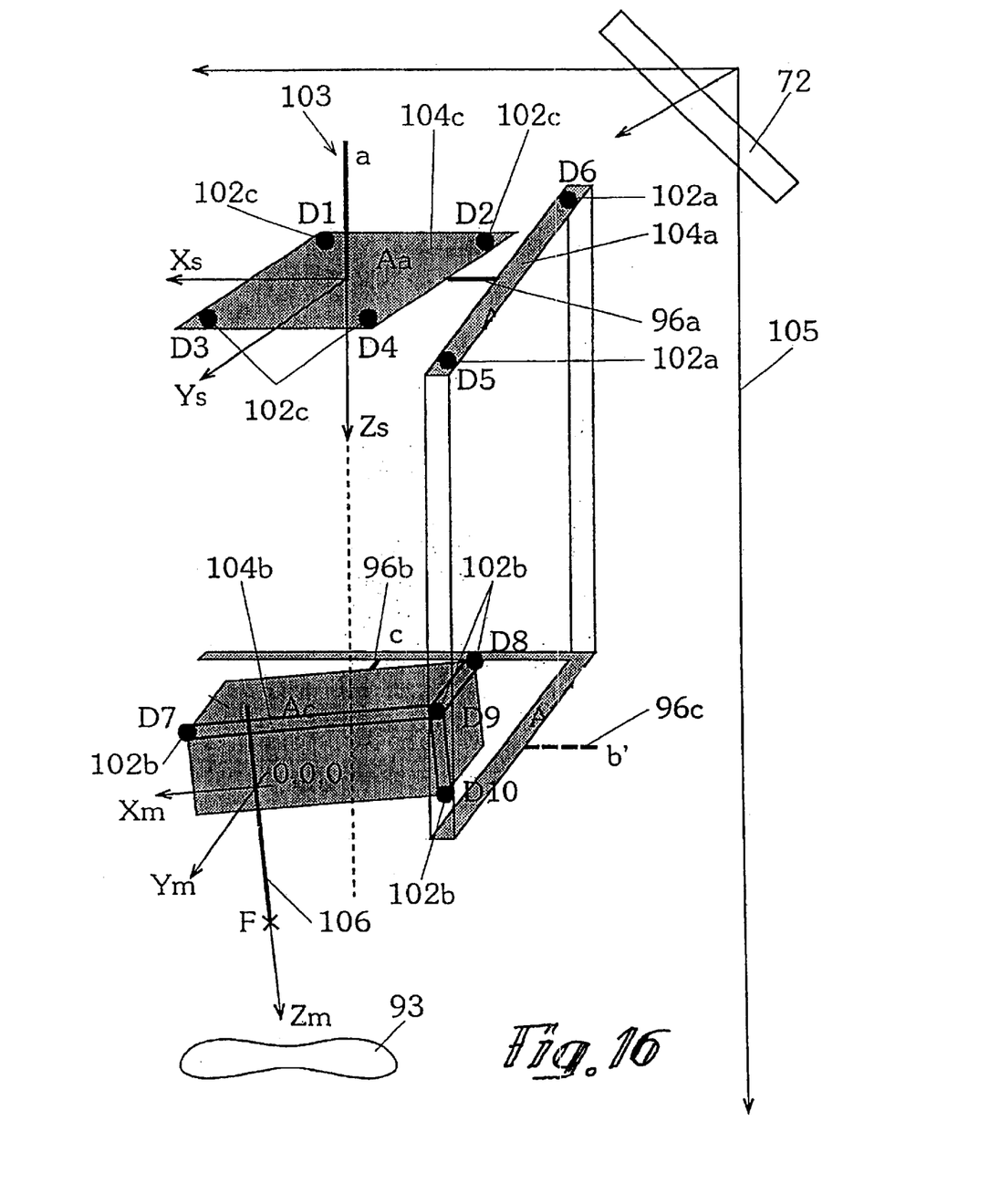
FIG. 16 symbolically shows a microscope assemblage having three components and geometrically arranged signal generators.

FIG. 16 symbolically shows a microscope such as that which can be mounted on an axis 96c on a stand. The microscope comprises three components 104a, 104b, and 104c that are independent of one another but joined to one another. Each of these components 104 is equipped with signal transducers 102 that can have a dual function. In the context of the one function, they can emit in coded form signals that provide information about the property of the corresponding component. These signals can be received by receiver 72 and can thus be used to identify the components that are added or taken away. Suitable signal transmitters are, for example, light-emitting diodes, ultrasonic transmitters, radio transmitters, or light reflectors that are excited by external light and make identification possible with a corresponding reflection datum. As a second variant function within the context of the invention, thanks to their geometrical arrangement these sensors can also contribute to the identification of specific positions and locations of the corresponding components. These positions and locations are also recorded via receiver 72 and converted by the computer into the corresponding balance data.

In a further independent step of the invention, in the context of an assemblage of this kind in which the sensing of the components and their properties and position is accomplished entirely from outside, it is possible conversely for the balancing drives also to be controlled from outside. The invention in this context provides for the signals received by receiver 72 to be processed, after conversion in the computer, into control signals that are sent back via a comparable transmitting system to the microscope or stand, in order to activate the corresponding balance positioning drives therein. In the specific FIG. 16, for example, it may be imagined that a pivoting of component 104a about axis 96c results in an imbalance that is compensated for by a pivoting of component 104c about axis 96a.

In no case is an imbalance measured in this context. On the contrary, according to the present invention in this example the change in the position of diodes D5 and D6 is detected by receiver 72, the imbalance is calculated, and the corresponding control signals are conveyed to a positioning motor (not depicted) to adjust part 104c in space, e.g. about or with axis 96a.

The positioning motor is either a stepper motor that travels to a predefined position or a motor of any kind that adjusts component 104c until the receiver, based on the modified position of diodes D1, D2, D3, and D4, detects the correct computationally ascertained balance position and terminates the adjustment operation. Component 104b is correspondingly equipped with diodes D7, D8, D9, and D10.

For illustration, FIG. 16 also depicts the corresponding coordinate systems 105, 106, and 103 as well as (symbolically) a specimen 93.

| | PARTS LIST |
|---|---|
| 1 | Pivot support |
| 2 | Electric motor |
| 3 | Electric motor |
| 4 | Electric motor |
| 5 | Stand foot |
| 6 | Support column |
| 7 | Bracing point |
| 8 | Bracing spring |
| 9 | Microscope |
| 10 | Computer |
| 11 | Interface |
| 12 | Interface |
| 13 | Interface |
| 14 | Interface |
| 15 | Angle sensor |
| 16 | Angle sensor |
| 17 | Angle sensor |
| 18 | Computer |
| 19 | Reading device |
| 20 | Electric motor |
| 21 | Counterweight |
| 22 | Component |
| 23 | Counterweight |
| 24 | Counterweight |
| 25 | Electric motor |
| 26 | Electric motor |
| 27 | Computer |
| 28 | Load |
| 29 | Angle sensor |
| 30 | Brake |
| 31 | Adjusting motor |
| 32 | Control line |
| 33 | Chip |
| 34 | Microscope |
| 35 | Component |
| 36 | Accessory part |
| 37 | Accessory part |
| 38 | Data medium |
| 39 | Data medium |
| 40 | Barcode data medium |
| 41 | Microchip data medium |
| 42 | Accessory part |
| 43 | Swiveling tube |
| 44 | Barcode data medium |
| 45 | Angle sensor |
| 46 | Information system |
| 47 | Accessory part |
| 48 | Computer |
| 49 | Balancing system |
| 50 | Balancing system |

-continued

PARTS LIST

| | |
|---|---|
| 51 | Keypad |
| 52 | Display |
| 53 | Intelligent component |
| 72 | Signal receiver and/or transmitter |
| 96a, 96b, 96c | Axes |
| 102a, 102b, 102c | Signal transducers |
| 104a, 104b, 104c | Component |
| D1 through D10 | Diodes (signal transmitters and/or receivers) |

What is claimed is:

1. A stand for supporting at least one component joined movably to said stand and a replaceable accessory detachably joined to said component, said stand comprising:

an automatically correctable balancing system having electrically controlled balancing mechanisms; and a computer for activating said balancing mechanisms;

wherein a computational model is implemented by said computer, and said accessory includes at least one readable data medium for storing balance correction data associated with said accessory for input to said computational model to calculate control commands for activating said balancing mechanisms.

2. The stand as defined in claim 1, wherein said component is joined to said stand for angular displacement about orthogonal pivot axes (XDA/YDA/ZDA), and said computational model controls a relative movement between an intersection (D) of said pivot axes and the center-of-gravity (SP) of said component in such a way that the intersection (D) of the pivot axes lies at the overall center of gravity (SP) of said component.

3. The stand as defined in claim 1, further comprising an automatic reading device in communication with said computer for reading said balance correction data stored by said at least one readable data medium.

4. The stand as defined in claim 1, wherein said balance correction data stored by said at least one readable data medium is readable by an operator, and said stand further comprises a data input unit in communication with said computer for enabling said operator to enter said balance correction data to said computer.

5. The stand as defined in claim 4, wherein said data input unit comprises a manually actuable keypad and a display.

6. The stand as defined in claim 3, further comprising an information system for receiving said balance correction data from said reading device and transmitting said balance correction data to said computer.

7. The stand as defined in claim 1, further comprising at least one sensor arranged to detect the position of said component relative to said stand, said at least one sensor being connected to said computer to convey position data relating to said component for input to said computational model in response to an adjustment in the position of said component relative to said stand.

8. The stand as defined in claim 7, wherein said at least one sensor includes an angle sensor for detecting angular displacement about a pivot axis.

9. The stand as defined in claim 7, wherein said replaceable accessory is movable relative to said component, and said computer receives position data relating to said accessory from a sensor arranged to detect the position of said accessory relative to said component for input to said computational model.

10. The stand as defined in claim 6, wherein said information system comprises a signal receiver that can receive from a distance signals that are emitted from signal transmitters on said component and said accessory part.

11. The stand as defined in claim 10, wherein said signal transmitters include a light-emitting diode.

12. The stand as defined in claim 10, wherein said signal transmitters include a ultrasonic transmitter.

13. The stand as defined in claim 10, wherein said signal transmitters include a radio transmitter.

14. The stand as defined in claim 10, wherein said signal transmitters include a light reflector excited by external light.

15. The stand as defined in claim 10, wherein said information system comprises telecommunication devices.

16. The stand as defined in claim 15, wherein said telecommunications devices include an infrared transceiver.

17. The stand as defined in claim 15, wherein said telecommunications devices include an ultrasound transceiver.

18. The stand as defined in claim 15, wherein said telecommunications devices include a radio transceiver.

19. The stand as defined in claim 6, wherein said at least one data medium comprises a microchip that automatically ascertains and transmits data relevant to balance to said information system.

20. The stand as defined in claim 19, wherein said data relative to balance is provided by an angle sensor associated with said accessory.

21. A method for automatically balancing out correctable balancing systems on a stand by means of a computer, said stand having a component movably joined thereto and said component having at least one replaceable accessory detachably joined thereto at an attachment base, said method comprising the steps of:

A) digitally sensing a weight and a center of gravity location of said at least one accessory with respect to said attachment base by means of an information system and conveying the sensed weight and center of gravity location to said computer for input to a corresponding computational model for correction; and B) directly activating electrical positioning motors associated with said balancing systems via said computer to achieve balancing.

22. The method as defined in claim 21, further comprising the steps of sensing the position of said at least one replaceable accessory and automatically entering said sensed position into said computer via said information system for input to said computational model.

23. The method as defined in claim 22, further comprising the step of providing a microchip having a logic system which automatically ascertains said position of said at least one replaceable accessory, and conveys said position via said information system directly into said computer.

24. The method as defined in claim 21, wherein said method comprises the steps of defining a local center-of-gravity coordinate system, calculating an actual center of gravity (SP) of said movable component in said local center-of-gravity coordinate system, computationally ascertaining the relative position of at least two pivot axes of said movable component, and activating said electrical positioning motors in such a way that an intersection (D) of said at least two pivot axes is brought into coincidence with said actual center of gravity (SP).

25. A method for automatically balancing out correctable balancing systems on a stand by means of a computer, said stand having a component movably joined thereto, and said component having at least one replaceable accessory detachably joined thereto at an attachment base, said method comprising the steps of:

A) indicating a weight and a center of gravity location of said at least one replaceable accessory on a readable data medium at said attachment base;

B) entering said weight and said center of gravity location into an information system connected to said computer, said information system conveying said weight and said center of gravity location to said computer for input to a corresponding computational model for correction; and C) directly activating electrical positioning motors associated with said balancing systems via said computer to achieve balancing.

26. The method as defined in claim 25, further comprising the steps of sensing the position of said at least one replaceable accessory and automatically entering said sensed position into said computer via said information system for input to said computational model.

27. The method as defined in claim 26, further comprising the step of providing a microchip having a logic system which automatically ascertains said position of said at least one replaceable accessory, and conveys said position via said information system directly into said computer.

28. The method as defined in claim 25, wherein said method comprises the steps of defining a local center-of-gravity coordinate system, calculating an actual center of gravity (SP) of said movable component in said local center-of-gravity coordinate system, computationally ascertaining the relative position of at least two pivot axes of said movable component, and activating said electrical positioning motors in such a way that an intersection (D) of said at least two pivot axes is brought into coincidence with said actual center of gravity (SP).

29. In a stand comprising an automatically correctable balancing system having electrically controlled balancing mechanisms and a computer for activating said balancing mechanisms, said stand having a component joined movably thereto, and said component having at least one replaceable accessory detachably joined thereto, the improvement comprising:

a computational model and an information system associated with said computer, said information system comprising a signal transmitter that transmits, from a distance, control signals from said computer to signal receivers for positioning motors operably connected to said accessory parts.

* * * * *